United States Patent

Bhotla et al.

(10) Patent No.: US 7,838,689 B2
(45) Date of Patent: Nov. 23, 2010

(54) METHOD FOR PRODUCING PHENOLPHTHALEIN COMPOUND USING IONIC LIQUID CATALYST COMPOSITION

(75) Inventors: Venkata Rama Narayanan Ganapathy Bhotla, Kamataka (IN); Dwairath Dhar, Kamataka (IN); Gurram Kishan, Kamataka (IN); Salkod Parameshwar Mallika, Kamataka (IN)

(73) Assignee: Sabic Innovative Plastics IP B.V. (NL)

( * ) Notice: Subject to any disclaimer, the term of this patent is extended or adjusted under 35 U.S.C. 154(b) by 234 days.

(21) Appl. No.: 12/239,952

(22) Filed: Sep. 29, 2008

(65) Prior Publication Data

US 2010/0081831 A1 Apr. 1, 2010

(51) Int. Cl.
*C07D 407/00* (2006.01)
(52) U.S. Cl. ..................................................... 549/308
(58) Field of Classification Search .................. 549/308
See application file for complete search history.

(56) References Cited

U.S. PATENT DOCUMENTS

| 2,192,485 | A | 3/1940 | Hubacher |
| 2,522,939 | A | 9/1950 | Gamrath |
| 2,522,940 | A | 9/1950 | Gamrath |
| 4,252,725 | A | 2/1981 | Prindle et al. |
| 6,573,405 | B1 | 6/2003 | Abbott et al. |
| 7,041,774 | B2 | 5/2006 | Kishan et al. |
| 7,045,482 | B2 | 5/2006 | Chun et al. |
| 2008/0177091 | A1 | 7/2008 | Basale et al. |

OTHER PUBLICATIONS

Xiao et al. Journal of Organometallic chemistry, 2005, 690, 3609-3613.*
Yin, et al., "High Regioselective Diels-Alder Reaction of Myrcene with Acrolein Catalyzed by Zinc-Containing Ionic Liquids," Adv. Synth. Catal., 347, (2005) pp. 137-142.
Bordoloi, et al., "Liquid-phase Veratrole Acylation and Toluenme Alkylation Over WOx/ZrO2 Solid Acid Catalysts," Journal of Molecular Catalysis A: Chemcial, 247, (2006) pp. 58-64.

* cited by examiner

*Primary Examiner*—D. Margaret Seaman
*Assistant Examiner*—Nizal S Chandrakumar
(74) *Attorney, Agent, or Firm*—Cantor Colburn LLP (57) ABSTRACT

A method for producing a phenolphthalein compound is disclosed, comprising: reacting a phenolic compound of the formula:

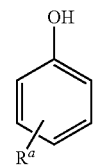

wherein $R^a$ is a hydrogen or a $C_1$-$C_{12}$ hydrocarbyl group, with a phthalic anhydride compound of the formula:

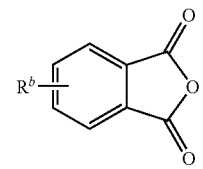

wherein $R^b$ is a hydrogen, a $C_1$-$C_{12}$ hydrocarbyl group, or a halogen, in the presence of an ionic liquid catalyst composition and a promoter to form a reaction mixture comprising a phenolphthalein compound of the formula:

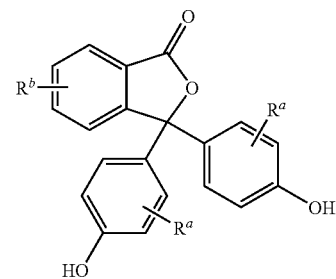

wherein each $R^a$ is independently a hydrogen or a $C_1$-$C_{12}$ hydrocarbyl group, and $R^b$ is a hydrogen, a $C_1$-$C_{12}$ hydrocarbyl group, or a halogen; wherein the ionic liquid catalyst composition comprises a combination of an ionic liquid and a metal halide wherein the metal is selected from the group consisting of a Group IIB, IIIA, VIII, or IVA metal, and a combination thereof.

21 Claims, 1 Drawing Sheet

FIG. 1

METHOD FOR PRODUCING PHENOLPHTHALEIN COMPOUND USING IONIC LIQUID CATALYST COMPOSITION

BACKGROUND

This disclosure is directed to methods of manufacturing phenolphthalein compounds, in particular methods using an ionic liquid catalyst composition.

Phenolphthalein compounds are useful as a starting material to make a wide range of products. For example, phenolphthalein compounds are important raw materials for the synthesis of 3,3-bis(4-hydroxyphenyl)phthalimidine and 2-hydrocarbyl-3,3-bis(4-hydroxyaryl)phthalimidines, in particular 2-phenyl-3,3-bis(4-hydroxyphenyl)phthalimidine (PPPBP). These phthalimidine compounds can be used in the manufacture of homopolycarbonates and copolycarbonates.

Phenolphthalein has been produced in a homogenous process in which phthalic anhydride is reacted with phenol in the presence of zinc chloride (ZnCl$_2$) as a catalyst. In U.S. Pat. No. 2,522,939, Gamrath disclosed improving this widely used process by the addition of chlorosulphonic acid as an activating agent (also referred to as a promoter) for the zinc chloride. This process has become commercially used because of the high purity, selectivity, and yield obtained.

Presently available manufacturing processes for phenolphthalein are time consuming and require large amounts of energy and chemicals, as well as complex equipment. U.S. patent application Ser. No. 11/626,671 discloses an improved method for producing and purifying phenolphthalein compounds on a commercial scale that requires fewer resources. In particular, after reacting a phthalic anhydride compound and a phenol compound in the presence of a catalyst and a promoter to form a reaction mixture comprising the phenolphthalein compound, the reaction mixture is treated with a solvent system to form a slurry. The slurry can then be filtered to obtain a solid material, which, after washing in water at an elevated temperature, comprises the phenolphthalein compound in high purity. This commercial process, however, still employs zinc chloride and chlorosulphonic acid to catalyze the reaction.

There are several significant challenges associated with processes for manufacturing a phenolphthalein compound using zinc chloride. In commercial practice, the zinc chloride is used in relatively large amounts, 0.6 mole of zinc chloride per mole of phthalic anhydride. The used catalyst must be separated from the reaction mixture after quenching of the reaction. The difficulty of separating the catalyst, which is used in slurry form, is increased because the slurry becomes very viscous over time. Importantly, the large amounts of used catalyst cannot be reused and must be disposed of safely.

It would be desirable to develop a process for the preparation of a phenolphthalein compound wherein the catalyst is more readily separated from the reaction mixture. It would further be desirable to develop a process for the preparation of a phenolphthalein compound that reduces waste generation, for example by allowing the catalyst to be reused. It would also be desirable if these processes provided phenolphthalein compounds of high purity.

BRIEF SUMMARY OF THE INVENTION

Some or all of the above-described deficiencies are addressed by a method for producing a phenolphthalein compound comprising reacting a phenolic compound of the formula:

wherein $R^a$ is a hydrogen or a $C_1$-$C_{12}$ hydrocarbyl group, with a phthalic anhydride compound of the formula:

wherein $R^b$ is a hydrogen, a $C_1$-$C_{12}$ hydrocarbyl group, or a halogen, in the presence of an ionic liquid catalyst composition and a promoter to form a reaction mixture comprising a phenolphthalein compound of the formula:

wherein each $R^a$ is independently a hydrogen or a $C_1$-$C_{12}$ hydrocarbyl group, and $R^b$ is a hydrogen, a $C_1$-$C_{12}$ hydrocarbyl group, or a halogen; wherein the ionic liquid catalyst composition comprises a combination of an ionic liquid and a metal halide wherein the metal is selected from the group consisting of a Group IIB, IIIA, VIII, or IVA metal, and a combination thereof.

In another embodiment, a method for producing a phenolphthalein compound comprises: reacting a phenolic compound of the formula:

wherein $R^a$ is a hydrogen or a $C_1$-$C_{12}$ hydrocarbyl group, with a phthalic anhydride compound of the formula:

wherein $R^b$ is a hydrogen, a $C_1$-$C_{12}$ hydrocarbyl group, or a halogen, in the presence of an ionic liquid catalyst composition and a promoter to form a reaction mixture comprising a phenolphthalein compound of the formula:

wherein each $R^a$ is independently a hydrogen or a $C_1$-$C_{12}$ hydrocarbyl group, and $R^b$ is a hydrogen, a $C_1$-$C_{12}$ hydrocarbyl group, or a halogen; wherein the ionic liquid catalyst composition comprises a combination of an ionic liquid and a metal halide wherein the metal is selected from the group consisting of zinc, iron, and a combination thereof

In another embodiment, a method for producing a phenolphthalein compound comprises: reacting a phenolic compound of the formula:

wherein $R^a$ is a hydrogen or a $C_1$-$C_{12}$ hydrocarbyl group, with a phthalic anhydride compound of the formula:

wherein $R^b$ is a hydrogen, a $C_1$-$C_{12}$ hydrocarbyl group, or a halogen, at a temperature of 100° C. to 175° C. in the presence of an ionic liquid catalyst composition and promoter to form a reaction mixture comprising a phenolphthalein compound of the formula:

wherein each $R^a$ is the same and is a hydrogen or a $C_1$-$C_{12}$ hydrocarbyl group, and $R^b$ is a hydrogen, a $C_1$-$C_{12}$ hydrocarbyl group, or a halogen; wherein the ionic liquid catalyst composition is present in an amount of 25 to 75 wt. % based on the weight of the reaction mixture and comprises a combination of an ammonium salt that is a liquid at 25° C., and zinc chloride; and wherein the reaction is carried out with stirring at a torque that, measured after 20 hours of reaction, is less than 3.0 Nm; and wherein the phenolphthalein compound is obtained in a yield of greater than or equal to 70 mol %, based on the moles of phthalic anhydride compound.

These and other features, aspects, and advantages of the present invention will become better understood when the following detailed description is read with reference to the accompanying figure.

DETAILED DESCRIPTION

The inventors hereof have discovered that use of an ionic liquid catalyst composition as both a liquid carrier and a catalyst in a process for the manufacture of phenolphthalein allows ready separation of the ionic liquid catalyst composition from the reaction mixture, thereby providing a more efficient and less wasteful process. It has further been unexpectedly found that the ionic liquid catalyst composition can be reused, which again provides a more efficient and less wasteful process. In a still further advantage, use of the ionic liquid catalyst composition can be used to provide phenolphthalein compounds of high purity.

The ionic liquid catalyst composition is formed by combining an ionic liquid and a metal halide. It is to be understood that the "ionic liquid catalyst composition" as used herein means the combination of the ionic liquid and the metal halide, and may or may not contain the ionic liquid and/or metal halide as individual constituents.

An "ionic liquid" as used herein means a salt having a melting point below 100° C., specifically below 50° C., and even more specifically at 23° C. (room temperature), and at about 1 atmosphere of pressure. The ionic liquids comprise a cation ionically associated with an anion. The cations are generally relatively large compared to simpler organic or inorganic cations, and contribute to the low melting point of the ionic liquids. Often, the cations are asymmetric, heterocyclic organic cations such as imidazolium, pyrazolium, pyridinium, pyrazinium, pyrimidinium, $C_1$-$C_{32}$ tetraalkylphosphonium, and $C_1$-$C_{32}$ tetraalkylammonium cations. The anions are generally smaller, and can be organic or inorganic, for example formate or a halide.

In a specific embodiment, the ionic liquid is an imidazolium salt of the formula:

wherein $R^1$ and $R^5$ are each independently a $C_1$-$C_{12}$ hydrocarbyl group, $R^2$, $R^3$, and $R^4$ are each independently a hydrogen or $C_1$-$C_{12}$ hydrocarbyl group, and $X^-$ is anion. In one embodiment, $R^1$ and $R^5$ are each a $C_1$-$C_{12}$ alkyl group, and $R^2$, $R^3$, and $R^4$ are each independently a hydrogen atom or an alkyl group, specifically an alkyl having from 1 to 6 carbon atoms, more specifically from 1 to 4 carbon atoms. In an embodiment, each of $R^1$, $R^2$, $R^3$, $R^4$, and $R^5$ is methyl.

Some specific examples of such imidazolium salts include 1-alkyl-3-methyl-imidazolium salts such as 1-butyl-3-methyl-imidazolium chloride or 1-ethyl-3-methyl-imidiazolium chloride.

In other embodiments, the ionic liquid is a pyrazolium salt of the formula:

wherein $R^6$ is a $C_1$-$C_{12}$ hydrocarbyl group, and $R^7$, $R^8$, and $R^9$ are each independently a hydrogen atom or a $C_1$-$C_{12}$ hydrocarbyl group, and $X^-$ is an anion.

In a specific embodiment, the ionic liquid comprises a pyrazolium cation wherein $R^6$ is an alkyl group, specifically an alkyl having from 1 to 8 carbon atoms, more specifically from 1 to 6 carbon atoms, even more specifically from 1 to 4 carbon atoms; and $R^7$, $R^8$, and $R^9$ are each independently a hydrogen atom or an alkyl group, specifically an alkyl having from 1 to 6 carbon atoms, and more specifically from 1 to 4 carbon atoms.

Another example of an ionic liquid used in making the ionic liquid catalyst composition is a pyridinium salt of the formula:

wherein $R^{11}$ is a $C_1$-$C_{12}$ hydrocarbyl group, each $R^{10}$ is independently a hydrogen or a $C_1$-$C_{12}$ hydrocarbyl group, and $X^-$ is an anion. A specific example of such an ionic liquid is N-butyl pyridinium chloride.

Still other examples of ionic liquids are pyrimidinium salts or pyrazinium salts of the formulas:

wherein $R_{12}$ is a $C_1$-$C_8$ hydrocarbyl group; each $R_{13}$ is independently a hydrogen or a $C_1$-$C_{12}$ hydrocarbyl group, n is 1 to 4, and $X^-$ is an anion.

In the pyrimidinium and pyrazinium salts, $R^{12}$ is specifically an alkyl group, specifically an alkyl having from 1 to 8 carbon atoms, and each $R^{13}$ is independently a hydrogen atom or an alkyl, specifically an alkyl having from 1 to 6 carbon atoms.

Still other examples of ionic liquids for use in the ionic liquid catalyst composition are ammonium and phosphonium salts of the formulas:

wherein $R^{14}$, $R^{15}$, $R^{16}$, and $R^{17}$ are each independently a $C_1$-$C_{12}$ hydrocarbyl group and $X^-$ is an anion.

Examples of these types of ionic liquids include tetraalkyl ammonium salts and tetraalkyl phosphonium salts, wherein each $R^{14}$, $R^{15}$, $R^{16}$, and $R^{17}$ is each the same alkyl group, specifically an alkyl having from 1 to 8 carbon atoms. Certain members of these classes possess ionic liquids properties similar to those of the organic cyclic cations.

The ionic liquid catalyst composition also comprises a combination comprising at least one of the foregoing ionic liquids.

In specific embodiments, the ionic liquid catalyst composition comprises an ionic liquid that is an heterocyclic imidazolium or pyridinium salt, specifically a 1,3-alkylimidazolium salt or a N-alkyl pyridinium salt, or a combination comprising at least one of the foregoing salts, wherein each alkyl group independently has 1 to 6 carbon atoms.

The anion ($X^-$) in the foregoing salts is an inorganic or organic anion, for example a tetrafluoroborate, nitrate, hexafluorophosphate, perchlorate, halide, phosphate, acetate, triflate (trifluoromethane sulfonate), sulfonate, methyl sulfonate, carboxylate, bis-trifluoromethyl sulfonamide, or a combination comprising at least one of the foregoing inorganic anions. More specifically, the inorganic anion is a halide, particularly when the cation is a 1,3-alkylimidazolium or a N-alkyl pyridinium.

The ionic liquids are prepared by a number of different methods known in the art. For example, 1-butyl-3-methylimidazolium chloride is prepared by boiling commercially available 1-methylimidazole with a 1-haloalkane such as 1-chlorobutane, followed by cooling, to obtain 1-butyl-3-methylimidazolium chloride. Similar preparation methods are employed to form other ionic liquids. For example a 1-alkyl-3-methylimidazolium bromide salt is prepared by heating 1-methylimidazole with a 1-bromoalkane, followed by cooling. To form a salt with a different anion, the 1-alkyl-3-methylimidazolium bromide salt, for example, is dissolved in a suitable water-insoluble organic solvent such as dichloromethane, and agitated in the presence of an aqueous solu- tion of the sodium salt of the desired anion, such as tetrafluoroborate ion. If the 1-alkyl group of the 1-alkyl-3-methylimidazolium cation is longer than about five carbons, the cation will remain in association with the dichloromethane, while the bromide ion will tend to migrate to the aqueous solution and be replaced by the tetrafluoroborate ion to maintain charge balance. This process avoids the necessity for an ion exchange column. The dichloromethane is removed by evaporation, if desired, to yield the pure 1-alkyl-3-methylimidazolium tetrafluoroborate salt.

Different metal halides are used to form the ionic liquid catalyst compositions. In some embodiments, the metal in the metal halide is a Group IIB, IIIA, VIII, or IVA metal such as aluminum, iron, zinc, tin or lead, and is specifically zinc. The halide is selected from any of fluoride, chloride, bromide, iodide, or a combination thereof, and is specifically chloride, e.g., $AlCl_3$ or $FeCl_3$. In one embodiment, zinc chloride is used.

The ionic liquid catalyst composition is obtained by simply combining the ionic liquid with the metal halide, preferably with agitation and at an elevated temperature. For example, the ionic liquid and the metal halide are mixed under an inert gas at 50 to 150° C. for 1 to 24 hours. The metal halide, typically a solid, dissolves gradually in the reaction mass to form a clear viscous liquid that is subsequently cooled and dried.

The molar ratio of the ionic liquid, specifically a quaternary ammonium salt, to the metal halide, specifically zinc chloride, can be 1:1 to 1:3. More specifically the molar ratio of the ionic liquid, specifically a quaternary ammonium salt, to the metal halide, specifically zinc chloride, can be 1:1.8 to 1:2.2.

The ionic liquid catalyst composition is used to provide a liquid carrier and catalyst for the reaction of a phenolic compound and a phthalic anhydride compound to produce a phenolphthalein compound. The phenolic compound is of formula (I):

(I)

wherein $R^a$ is a hydrogen or $C_1$-$C_{12}$ hydrocarbyl group, specifically a hydrogen, $C_1$-$C_3$ alkyl, or $C_1$-$C_3$ alkoxy. In one embodiment, $R^a$ is a hydrogen.

The phthalic anhydride compound is of formula (II):

(II)

wherein $R^b$ is a hydrogen, a $C_1$-$C_{12}$ hydrocarbyl group, or a halogen, specifically a hydrogen, $C_1$-$C_3$ alkyl, $C_1$-$C_3$ alkoxy, bromine, or chlorine. In one embodiment, $R^b$ is a hydrogen.

The phenolphthalein compound produced in the reaction is of formula (III):

(III)

wherein each $R^a$ is independently a hydrogen or a $C_1$-$C_{12}$ hydrocarbyl group; and $R^b$ is a hydrogen, a $C_1$-$C_{12}$ hydrocarbyl group, or a halogen. In a specific embodiment, each $R^a$ is the same and is a hydrogen, $C_1$-$C_3$ alkyl, or $C_1$-$C_3$ alkoxy; and $R^b$ is hydrogen, $C_1$-$C_3$ alkyl, $C_1$-$C_3$ alkoxy, bromine, or chlorine. In another embodiment, each $R^a$ is a hydrogen, and $R^b$ is a hydrogen.

The phenolic compound is reacted with the phthalic anhydride compound in the presence of the ionic liquid catalyst composition and a promoter. Exemplary promoters include chlorosulphonic acid, a $C_1$-$C_{12}$ alkyl sulphonic acid, a $C_6$-$C_{12}$ aryl sulphonic acid, a $C_1$-$C_{12}$ alkyl $C_6$-$C_{12}$ aryl sulphonic acid, a halogenated $C_1$-$C_{12}$ alkyl sulphonic acid, a halogenated $C_6$-$C_{12}$ aryl sulphonic acid, a halogenated $C_1$-$C_{12}$ alkyl $C_6$-$C_{12}$ aryl sulphonic acid, trichloroacetic acid, triflic acid, boron trifluoride, and combinations comprising at least one of the foregoing promoters. Specific promoters that can be used include chlorosulphonic acid, methanesulphonic acid, dodecylbenzenesulphonic acid, triflic acid, boron trifluoride, p-toluene sulphonyl chloride, and combinations comprising at least one of the foregoing. In one embodiment, the promoter is chlorosulphonic acid.

The reaction is typically carried out using a stoichiometric excess of the phenolic compound relative to the phthalic anhydride. In one embodiment, the reaction is carried out using a molar ratio of the phthalic anhydride compound to the phenolic compound of 1:2.1 to 1:10, specifically 1:2.1 to 1:3, more specifically 1:2.1 to 1:2.5.

The amount of the ionic liquid catalyst composition used in the reaction varies, depending on the type of ionic liquid catalyst composition, its activity, the desired time for the reaction, and like considerations. In general, the amount of the ionic liquid catalyst composition is 25 to 100 wt. %, based on the weight of the phenolic compound and the phthalic anhydride compound. Other components in the reaction mixture, in addition to the ionic liquid and the metal halide, dissolve in the ionic liquid catalyst composition, such as the promoter or organic solvents, but are excluded for determining weight percent. More specifically, the ionic liquid catalyst composition is present in an amount of 25 to 75 wt. % based on the weight of phenolic compound and the phthalic anhydride compound.

The promoter is present in the amount of up to 0.01 to 0.6 molar equivalents, based on the moles of phthalic anhydride. Specifically, chlorosulphonic acid is present in an amount of 0.05 to 0.5 molar equivalents, more specifically 0.1 to 0.3 molar equivalents, based on the moles of phthalic anhydride compound.

The conditions for the reaction vary, depending on the particular phenolic compound, phthalic anhydride compound, ionic liquid catalyst composition, and promoter. In one embodiment, the reaction is conducted at elevated temperature, for example, a temperature of 75° C. to 175° C., specifically 100 to 175° C., more specifically 110 to 165° C., for a reaction time of 10 to 100 hours, specifically 20 to 70 hours, more specifically 30 to 60 hours. The progress of the reaction can be followed by numerous analytical techniques such as gas chromatography or high-pressure liquid chromatography (HPLC).

Following reaction, the reaction mixture comprising the product, the phenolphthalein compound, is typically quenched. Quenching can be, for example, by the addition of a non-polar solvent such as toluene or a mixture of a polar and non-polar solvent, for example, toluene and methanol. The phenolphthalein compound is separated from the ionic liquid catalyst composition, following reaction and quenching with a solvent in which the phenolphthalein is not soluble. A solid-containing portion of the reaction mixture, in the form of a viscous mass, comprising solidified phenolphthalein compound can be obtained by decantation to remove a liquid portion of the reaction mixture comprising the ionic liquid composition. The remaining solid-containing portion comprising solidified phenolphthalein compound is mixed with an aqueous solvent such as distilled water, filtered, and washed with further aqueous solvent. The ionic liquid catalyst composition is recovered from a mother liquor, which as used herein refers to the liquid portion of the reaction mixture remaining after removal of the solid-containing portion comprising the phenolphthalein compound. The mother liquor can be separated from the solid-containing portion by decanting. Recovery of the ionic liquid catalyst comprises removing organic solvent from the mother liquor. The ionic liquid catalyst composition can then be reused, in whole or in part, depending on the amount of ionic liquid catalyst recovered. Fresh (i.e., unused) ionic liquid catalyst can be added to the recovered ionic liquid catalyst. For example, an ionic liquid catalyst comprising 50 to 70% of recovered catalyst and 30-50 wt. % of unused catalyst can be employed.

In some embodiments, the product phenolphthalein compound is obtained at a purity of at greater than or equal to 80 wt. %, specifically 90 to 99 wt. %, more specifically 94 to 97 wt. %, based on the total weight of crude phenolphthalein (reaction product obtained after solidification in the presence of an antisolvent such as toluene and washing of the product with water or other solvent). The phenolphthalein compound is obtained in a yield of greater than or equal to 70 mol %, specifically greater than or equal to 80 mol %, based on the moles of phthalic anhydride compound. In one embodiment, the phenolphthalein compound is obtained both at a purity of greater than 80 wt. %, specifically 90 to 99 wt. %, more specifically 94 to 97 wt. %, based on the total weight of crude phenolphthalein product, and in a yield of greater than or equal to 70 mol %, specifically greater than or equal to 80 mol %, based on the moles of phthalic anhydride compound.

In a particularly advantageous embodiment, the ionic liquid catalyst composition is reused. Specifically, the ionic liquid catalyst composition is separated from the reaction mixture comprising the phenolphthalein compound and reused for at least one more cycle, for a total of 2 to 4 cycles, specifically 2 to 3 cycles, wherein the first use of the fresh catalyst is considered a first cycle.

All or part of the foregoing method can be conducted as a batch or continuous process, for example, using a continuous stirred-tank reaction (CSTR). The ease of separating the ionic liquid catalyst composition and its regeneration allows a continuous process, as compared to the use of zinc chloride alone, which typically involves a viscous slurry.

The embodiments described herein provide several significant advantages. The method using an ionic liquid catalyst composition to provide both liquid carrier and catalyst provides excellent selectivity and yield, comparable to that obtained by the use of a catalyst system comprising zinc chloride in a solvent slurry. In addition, however, it is environmentally superior to the use of zinc chloride in a solvent slurry, since it reduces the effluent disposal problem. After completion of the reaction, the ionic liquid catalyst composition can be readily separated from the phenolphthalein in the reaction mixture, for example by, simple decantation]. The ionic liquid catalyst composition is reused (no regeneration is necessary) for at least one more reaction cycle. The original unused ("fresh") activity is substantially retained. In some embodiments, unused ionic liquid catalyst composition can be added to reused ionic liquid catalyst composition to rejuvenate its catalytic activity or other properties.

Importantly, the reaction is carried out with improved stirrability. In one embodiment, the method comprises stirring at a torque that, measured after 20 hours of reaction, is less than 3.0 Nm (Newton-meters), specifically 1.0-2.5 Nm, more specifically 1.0-2.0 Nm. The method also comprises stirring at a torque that, measured after 10 hours of reaction, is less than 3.0 Nm, specifically 1.0 to 2.5 Nm, and more specifically 1.0 to 2.0 Nm. Thus, stirrability can be improved by the use of an ionic liquid catalyst composition throughout the length of the process, with increasingly superior results the longer the reaction is extended. The present catalyst system allows the reaction to go to completion for a longer period of time than possible when using a metal halide such as zinc chloride without the use of an ionic liquid.

The phenolphthalein compound of formula (III) can be used as a starting material to make a wide range of products. For example, the phenolphthalein compound of formula (III) wherein each $R^a$ and $R^b$ are hydrogen can be converted to PPPBP by known methods, and then used as a monomer in the manufacture of homopolycarbonates and copolycarbonates.

The above-described processes are further illustrated by the following non-limiting examples.

EXAMPLES

Preparation of Ionic Liquid Catalyst Composition

A mixture of 1-butyl-3-methyl-imidazolium chloride (10.0 g, 0.057 moles) was stirred using a mechanical stirrer in a three-necked round bottom flask with anhydrous zinc chloride ($ZnCl_2$, 15.57 g, 0.114 moles) under nitrogen at 100° C. for 12 hours. The solid $ZnCl_2$ dissolved gradually in the reaction mass to form a clear viscous liquid. After the reaction the temperature was brought down to room temperature, and the reaction mass was dried under vacuum. The yield of the zinc-chloride-modified ionic liquid was almost 100 percent.

Methods of Analysis

In order to measure the progress of the reaction, HPLC analysis was generally carried out by using a solution of about 25 milligrams of a sample from the reaction mixture dissolved in about 50 milliliters of acetonitrile:0.05% aqueous $H_3PO_4$ (70:30 v:v). The HPLC instrument was equipped with a C8 (reverse phase) column maintained at a temperature of 40° C. and an ultraviolet detector capable of detecting components at a wavelength of 225 nanometers. A solvent mixture of acetonitrile and water with 0.02% $H_3PO_4$ of gradient elution was used. The flow rate was maintained at 1 milliliter per minute. Area percent purity was computed from the area value for each peak detected in the chromatogram divided by the total area from all peaks detected. To measure weight percent assay, calibration curves for phenol, phthalic anhydride, and phenolphthalein were first generated. Then the weight percent of a given component in a sample was calculated using these calibration curves.

The weight percent (wt. %) assay of isolated solid phenolphthalein was computed by calculating the phenol and phthalic anhydride content using suitable calibration graphs, and all other impurities ("others") were calculated using the response factor of phenolphthalein. The purity of the phenolphthalein was calculated by subtracting the amount of phenol, phthalic anhydride, and "others" from 100.

Example 1

Comparative Preparation of Phenolphthalein Using Zinc Chloride

In a 500 mL round bottom flask equipped with a mechanical stirrer, thermometer, nitrogen inlet, and reflux condenser, 18.5 g of phthalic anhydride (0.125 moles) and 27.6 g of phenol (2.25 molar equivalents based on phthalic anhydride) were charged followed by 10.0 g of zinc chloride (0.6 molar equivalents based on phthalic anhydride) and 2.91 g chlorosulphonic acid (0.2 molar equivalents based on phthalic anhydride), while maintaining the round bottom flask in a nitrogen atmosphere at 50 to 60° C. The reaction mixture was then heated with stirring at 120° C. (bath temperature) for 18 hours. Over the course of the reaction (18 hours), the reaction mass progressively turned from orange to brownish orange to deep brown. After 18 hours, the reaction mixture was cooled with stirring to 85° C. To the reaction mixture at 85° C., 160 mL of 95:5 toluene:methanol mixture was added and stirring was continued for one hour. After one hour, the reaction mixture was cooled to room temperature, solid phenolphthalein was filtered, washed with 100 mL hot water, and dried at 100° C. The yield of crude phenolphthalein was 37 g (about 93 mol %) and the purity was 95 wt. %.

Preparation of Phenolphthalein Using Zinc-Containing Ionic Liquid Catalyst Compositions In a 250 mL round bottom flask equipped with mechanical stirrer, thermometer, nitrogen inlet and reflux condenser, 10.0 g of phthalic anhydride (0.067 moles) and 15 g of ionic liquid catalyst composition (zinc chloride and 1-butyl-3-methyl-imidazolium) (60 wt. % based on total weight of reactants) were charged to the round bottom flask followed by 14.3 g phenol (2.25 molar equivalents based on phthalic anhydride) and 1.9 g chlorosulphonic acid (0.2 molar equivalents based on phthalic anhydride), while maintaining the round bottom flask in a nitrogen atmosphere at 50 to 60° C. The reaction mixture was then heated with stirring at 120° C. (bath temperature). Over the course of the reaction (24 hours), the reaction mass progressively turned from orange to brownish orange to deep brown. After 24 hours, the reaction mixture comprising phenolphthalein was then quenched with 150 mL toluene. The viscous mass produced by the addition of toluene was stirred at 85° C. for about 30 min. The supernatant (containing the ionic liquid catalyst composition, toluene, and unreacted starting material) was decanted and the remaining viscous mass was then heated with 150 mL water and stirred at 85° C. for about 30 min. The solidified phenolphthalein was filtered while hot and washed until the supernatant was neutral with cold, distilled water to obtain crude phenolphthalein. The resulting brownish yellow solid was dried under vacuum at 100° C. overnight. The yield of crude phenolphthalein was 18.7 g (89 mol %) and the purity was 96.08 wt. %.

The reaction was repeated for various ionic liquid catalyst compositions and reaction conditions as shown in Table 1. The results are also shown in Table 1.

TABLE 1

| Sample No. | Amount of ionic liquid catalyst composition | Composition | Reaction Conditions | Phthalic Anhydride | Phenol | Total impurities | Yield (mol %) | Purity (wt. %) |
|---|---|---|---|---|---|---|---|---|
| 1 | 50 wt. % | Imidazolium chloride/ZnCl$_2$ | 120° C. 24 hrs | 0.16 | 0.11 | 4.66 | 76.00 | 95.34 |
| 2 | 60 wt. % | Imidazolium chloride/ZnCl$_2$ | 120° C. 24 hrs | 0.13 | 0.12 | 3.92 | 89.00 | 96.08 |
| 3 | 50 wt. % | Imidazolium chloride/ZnCl$_2$ | 140° C. 24 hrs | 0.17 | 0.47 | 6.57 | 88.00 | 93.43 |
| 4 | 50 wt. % | Tetraethyl ammonium chloride/ZnCl$_2$ | 120° C. 24 hrs | 2.30 | 1.20 | 7.80 | 25.00 | 91.80 |
| 5* | 50 wt. % | Imidazolium chloride and SO$_3$H$^-$ | 140° C. 24 hrs | 1.60 | 0.30 | 13.50 | 29.00 | 86.50 |

*Comparative Example

As shown in Table 1, use of the ionic liquid catalyst composition comprising zinc-chloride-modified 1-butyl-3-methyl-imidazolium chloride was tested as a catalyst for making phenolphthalein under different conditions. When used at a loading of 50 wt. %, the product was isolated at a yield of 76 mol % and a purity of 95.3 wt. % (by HPLC). Increasing the amount of the ionic liquid catalyst composition to 60 wt. % increased the product yield to 89 mol % and increased product purity to 96.1 wt. %. Increasing the temperature of reaction to 140° C. also improved the yield.

In comparison, use of an ionic liquid catalyst composition containing methyl imidazolium-SO$_3$H$^-$ (derived from 1-methyl imidazole and 1,4-butanesulphone, and without zinc) in the same process at 140° C. gave phenolphthalein with lower yield (29 mol %) and lower purity (86.53 wt. %).

Example 2

Figure 1:
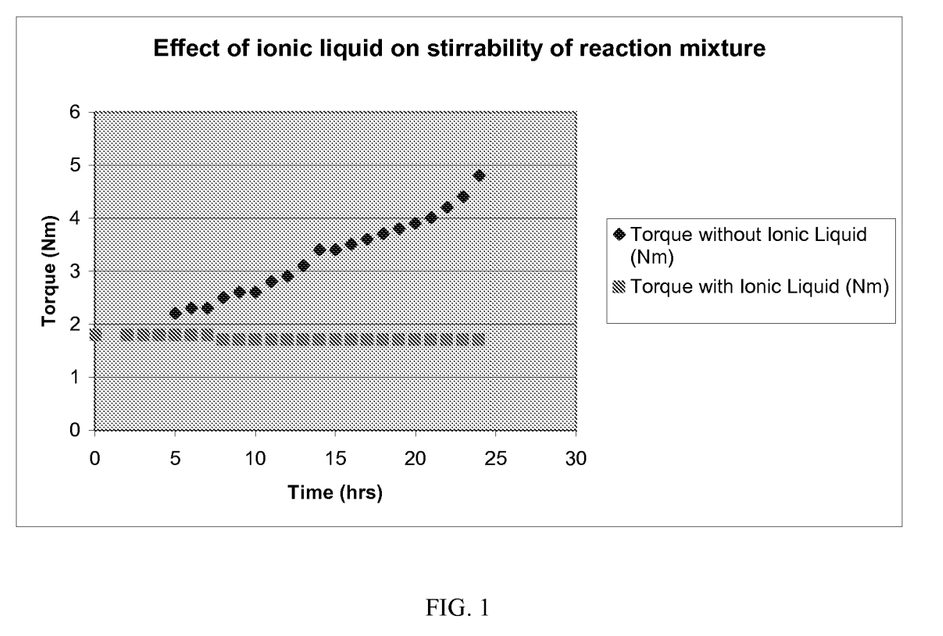
The FIGURE shows the effect of an ionic liquid catalyst composition on stirrability of a reaction mixture in the preparation of a phenolphthalein compound.

This example illustrates a method of making phenolphthalein using reused ionic liquid catalyst composition. Following the procedure in Example 1, toluene was removed from the supernatant of Example 1 using a Rotovac® evaporator to recover 7.5 g of residue containing the ionic liquid catalyst composition. This residue was placed in a 250 mL round bottom flask equipped with mechanical stirrer, thermometer, nitrogen inlet and reflux condenser. To this residue, 10.0 g of phthalic anhydride (0.067 moles) and 7.5 g of fresh ionic liquid catalyst composition (zinc-chloride modified 1-butyl-3-methyl-imidazolium chloride) (30 wt. % based on total weight of reactants) were charged, followed by 14.3 g phenol (2.25 molar equivalents based on phthalic anhydride) and 1.9 g chlorosulphonic acid (0.2 molar equivalents based on phthalic anhydride), while maintaining the round bottom flask in a nitrogen atmosphere at 50 to 60° C. The reaction mixture was then heated with stirring at 120° C. (bath temperature). Over the course of the reaction (24 hours), the reaction mass progressively turned from orange to brownish orange to deep brown. The reaction was then quenched with 150 mL toluene. The quenched mass was stirred at 85° C. for about 30 min. Again, the supernatant containing the toluene and ionic liquid catalyst composition was decanted away, and the remaining viscous mass was then mixed with 150 mL water, followed by stirring at 85° C. for about 30 min. The resulting mixture, containing the phenolphthalein, was filtered while hot and washed to neutral with cold distilled water. The resulting brownish yellow solid was dried under vacuum at 100° C. overnight. The yield of crude phenolphthalein was 14 g (65 mol %), and the purity was 95.58 wt. %. The results are shown in Table 2.

considerably. When an ionic liquid catalyst composition is used, the torque remains constant throughout the progress of the reaction.

The singular forms "a," "an," and "the" include plural referents unless the context clearly dictates otherwise. Unless defined otherwise, technical and scientific terms used herein have the same meaning as is commonly understood by one of skill in the art to which this invention belongs. The endpoints of all ranges directed to the same component or property are inclusive and independently combinable (e.g., ranges of "less than or equal to about 25 wt. %, or, more specifically, about 5 wt. % to about 20 wt. %," is inclusive of the endpoints and all intermediate values of the ranges of "about 5 wt. % to about 25 wt. %," etc.).

Compounds, including salt forms, are described using standard nomenclature. For example, any position not substituted by any indicated group is understood to have its valency filled by a bond as indicated, or a hydrogen atom. A dash ("—") that is not between two letters or symbols is used to

TABLE 2

| No. | Ionic Liquid Catalyst Condition | Composition | Reaction Conditions | Phthalic Anhydride | Phenol | Total Impurities | Yield (mol %) | Purity (wt. %) |
|---|---|---|---|---|---|---|---|---|
| 2 | Unused | Imidazolium chloride/ZnCl$_2$ | 120° C. 24 hrs | 0.13 | 0.12 | 3.92 | 89.00 | 96.08 |
| 6 | Partially Reused | Imidazolium chloride/ZnCl$_2$ | 120° C. 24 hrs | 0.73 | 0.11 | 4.42 | 65.00 | 95.58 |

Based on the results in Table 2, it can be seen that when fresh catalyst was used at a loading of 60 wt. %, the product phenolphthalein was isolated at a yield of 89.0 mol % and a purity of 96.1 wt. %. Recovered and reused catalyst gave phenolphthalein with a yield 65.0 mol % and purity 95.58 wt. %. These results indicate that ionic liquid composition can be partially recycled, with a drop in yield (activity) but similar product purity (selectivity). It is also possible to recover more of the ionic liquid catalyst, for example by additional toluene extractions.

Example 3

This Example shows the effect of using the ionic liquid catalyst composition on the stirrability of the reaction mixture during the preparation of phenolphthalein, compared to a method without the use of the ionic liquid catalyst composition.

The reaction was carried out as described in Example 1 above. A mechanical overhead stirrer with digital display for torque, commercially available from Heidolph Germany, was used. The results are shown in FIG. 1. As can be seen from FIG. 1, in the comparative process using only ZnCl$_2$ catalyst, the torque increases with time for up to 24 hours (the reaction study time). The stirrability of the reaction mass is hindered and the torque needed to stir the reaction mass increases indicate a point of attachment for a substituent. For example, —CHO is attached through carbon of the carbonyl group.

As used herein, the term "hydrocarbyl" is defined as a monovalent moiety formed by removing a hydrogen atom from a hydrocarbon. Representative hydrocarbyls are alkyl groups having 1 to 12 carbon atoms, such as methyl, ethyl, propyl, butyl, pentyl, hexyl, heptyl, octyl, nonyl, undecyl, decyl, dodecyl, and the isomeric forms thereof; aryl groups having 6 to 12 carbon atoms, such as ring-substituted and ring-unsubstituted forms of phenyl, tolyl, xylyl, naphthyl, biphenyl, and the like; aralkyl groups having 7 to 12 carbon atoms, such as ring-substituted and ring-unsubstituted forms of benzyl, phenethyl, phenpropyl, phenbutyl, and the like; and cycloalkyl groups, such as cyclopropyl, cyclobutyl, cyclopentyl, cyclohexyl, cycloheptyl, cyclooctyl, and the like, as well as the corresponding oxides of the foregoing groups. The term "aryl" as used herein refers to an aromatic monovalent group containing only carbon in the aromatic ring or rings.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While various embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

We claim:

1. A method for producing a phenolphthalein compound comprising:
reacting a phenolic compound of the formula:

wherein $R^a$ is a hydrogen or a $C_1$-$C_{12}$ hydrocarbyl group, with a phthalic anhydride compound of the formula:

wherein $R^b$ is a hydrogen, a $C_1$-$C_{12}$ hydrocarbyl group, or a halogen, in the presence of an ionic liquid catalyst composition and a promoter to form a reaction mixture comprising a phenolphthalein compound of the formula:

wherein each $R^a$ is independently a hydrogen or a $C_1$-$C_{12}$ hydrocarbyl group, and $R^b$ is a hydrogen, a $C_1$-$C_{12}$ hydrocarbyl group, or a halogen;

wherein the ionic liquid catalyst composition comprises a combination of an ionic liquid and a metal halide wherein the metal is selected from the group consisting of a Group IIB, IIIA, VIII, or IVA metal, and a combination thereof.

2. The method of claim 1 wherein the ionic liquid is a quaternary organic ammonium salt that is a liquid at 25° C.

3. The method of claim 1 wherein the ionic liquid is an imidazolium salt, pyrazolium salt, pyridinium salt, pyrimidinium salt, pyrazinium salt, $C_1$-$C_{32}$ tetraalkyl ammonium salt, $C_1$-$C_{32}$ tetraalkyl phosphonium salt, or a combination comprising at least one of the foregoing salts, wherein each of the foregoing salts is a liquid at 25° C.

4. The method of claim 1 wherein the ionic liquid is:
a salt of the formula:

wherein $R^1$ and $R^5$ are independently a $C_1$-$C_8$ hydrocarbyl group, $R^2$, $R^3$, and $R^4$ are each independently a hydrogen or a $C_1$-$C_8$ hydrocarbyl group, and $X^-$ is anion;

a salt of the formula:

wherein $R_6$ is a $C_1$-$C_8$ hydrocarbyl, $R_7$, $R_8$, and $R_9$ are each independently a hydrogen atom or a $C_1$-$C_8$ hydrocarbyl group, and $X^-$ is an anion;

a salt of the formula:

wherein $R^{11}$ is a $C_1$-$C_8$ hydrocarbyl group, each $R^{10}$ is independently a hydrogen or a $C_1$-$C_8$ hydrocarbyl group, and $X^-$ is an anion;

a salt of the formula:

wherein $R^{12}$ is a $C_1$-$C_8$ hydrocarbyl group, each $R^{13}$ is independently a hydrogen or $C_1$-$C_8$ hydrocarbyl group, n is 1 to 4, and $X^-$ is an anion, a salt of the formula:

wherein $R^{14}$, $R^{15}$, $R^{16}$, and $R^{17}$ are each independently a $C_1$-$C_8$ hydrocarbyl group, and $X^-$ is an anion; or
a combination comprising at least one of the foregoing salts.

5. The method of claim 4 wherein $X^-$ in each salt is independently a fluoride, bromide, or chloride.

6. The method of claim 1 wherein the ionic liquid is a 1,3-alkylimidazolium salt, a N-alkyl pyridinium salt, or a combination comprising at least one of the foregoing salts, wherein each alkyl independently has 1 to 6 carbon atoms.

7. The method of claim 1 wherein the molar ratio of the ionic liquid to the metal halide is 1:1 to 1:3.

8. The method of claim 1 wherein the molar ratio of the ionic liquid to the metal halide is 1:1.8 to 1:2.2.

9. The method of claim 1 wherein the metal halide is zinc chloride.

10. The method of claim 1 wherein the promoter is chlorosulphonic acid, a $C_1$-$C_{12}$ alkyl sulphonic acid, a $C_6$-$C_{12}$ aryl sulphonic acid, a $C_1$-$C_{12}$ alkyl $C_6$-$C_{12}$ aryl sulphonic acid, a halogenated $C_1$-$C_{12}$ alkyl sulphonic acid, a halogenated $C_6C_{12}$ aryl sulphonic acid, a halogenated $C_1$-$C_{12}$ alkyl $C_6$-$C_{12}$ aryl sulphonic acid, trichloroacetic acid, triflic acid, boron trifluoride, or a combination comprising at least one of the foregoing promoters.

11. The method of claim 10 wherein the promoter is chlorosulphonic acid.

12. The method of claim 1 wherein the reaction is conducted with stirring and wherein, as measured after reaction for 20 hours, stirring is at a torque that is less than 3.0 Nm.

13. The method of claim 1 wherein, following reaction, the reaction is quenched with an organic solvent to form a solid phase comprising the phenolphthalein compound and a liquid phase comprising the ionic liquid catalyst composition, the solid phase is separated from a liquid phase, and the ionic liquid catalyst composition is recovered from the liquid phase.

14. The method of claim 13, further comprising reusing the recovered ionic liquid catalyst composition for at least one additional reaction cycle to form the phenolphthalein compound.

15. The method of claim 14 wherein unused ionic liquid catalyst composition is mixed with the recovered used ionic liquid catalyst composition in the at least one additional reaction cycle.

16. The method of claim 13, wherein the phenolphthalein compound in the separated solid phase is mixed with an aqueous solvent, filtered, and washed with aqueous solvent to obtain a purified phenolphthalein compound in a yield of greater than or equal to 70 mol %, based on the moles of phthalic anhydride compound.

17. The method of claim 1 further comprising converting the phenolphthalein compound to 2-phenyl-3,3-bis(4-hydroxyphenyl)phthalimidine.

18. The method of claim 1 further comprising polymerizing the 2-phenyl-3,3-bis (4-hydroxyphenyl)phthalimidine to form a polycarbonate.

19. A method for producing a phenolphthalein compound, comprising:

reacting a phenolic compound of the formula:

wherein $R^a$ is a hydrogen or a $C_1$-$C_{12}$ hydrocarbyl group, with a phthalic anhydride compound of the formula:

wherein $R^b$ is a hydrogen, a $C_1$-$C_{12}$ hydrocarbyl group, or a halogen, in the presence of an ionic liquid catalyst composition and a promoter to form a reaction mixture comprising a phenolphthalein compound of the formula:

wherein each $R^a$ is independently a hydrogen or a $C_1$-$C_{12}$ hydrocarbyl group, and $R^b$ is a hydrogen, a $C_1$-$C_{12}$ hydrocarbyl group, or a halogen;
wherein the ionic liquid catalyst composition comprises a combination of an ionic liquid and a metal halide wherein the metal is selected from the group consisting of zinc, iron, and a combination thereof.

20. A method for producing a phenolphthalein compound comprising:

reacting a phenolic compound of the formula:

wherein $R^a$ is a hydrogen or a $C_1$-$C_{12}$ hydrocarbyl group, with a phthalic anhydride compound of the formula:

wherein $R^b$ is a hydrogen, a $C_1$-$C_{12}$ hydrocarbyl group, or a halogen, at a temperature of 100° C. to 175° C. in the presence of an ionic liquid catalyst composition and promoter to form a reaction mixture comprising a phenolphthalein compound of the formula:

wherein each $R^a$ is the same and is a hydrogen or a $C_1$-$C_{12}$ hydrocarbyl group, and $R^b$ is a hydrogen, a $C_1$-$C_{12}$ hydrocarbyl group, or a halogen;

wherein the ionic liquid catalyst composition is present in an amount of 25 to 75 wt. % based on the weight of the reaction mixture and comprises a combination of an ammonium salt that is a liquid at 25° C., and zinc chloride; and wherein the reaction is carried out with stirring at a torque that, measured after 20 hours of reaction, is less than 3.0 Nm; and wherein the phenolphthalein compound is obtained in a yield of greater than or equal to 70 mol %, based on the moles of phthalic anhydride compound.

21. The method of claim 20 wherein the phenolphthalein compound obtained has a purity of greater than or equal to 80 weight percent, based on the weight of the precipitate.

* * * * *